(12) United States Patent
Anitua Aldecoa

(10) Patent No.: US 9,241,776 B2
(45) Date of Patent: Jan. 26, 2016

(54) IMPLANT EXTRACTION TOOL

(75) Inventor: Eduardo Anitua Aldecoa, Vitoria (ES)

(73) Assignee: BIOTECHNOLOGY INSTITUTE, I MAS D, S.L., Vitoria (ES)

( * ) Notice: Subject to any disclaimer, the term of this patent is extended or adjusted under 35 U.S.C. 154(b) by 236 days.

(21) Appl. No.: 13/000,263

(22) PCT Filed: Jun. 18, 2009

(86) PCT No.: PCT/ES2009/000335
§ 371 (c)(1),
(2), (4) Date: Mar. 24, 2011

(87) PCT Pub. No.: WO2009/153372
PCT Pub. Date: Dec. 23, 2009

(65) Prior Publication Data
US 2011/0172673 A1    Jul. 14, 2011

Related U.S. Application Data

(63) Continuation-in-part of application No. 12/198,213, filed on Aug. 26, 2008, now abandoned.

(30) Foreign Application Priority Data

Jun. 20, 2008    (ES) .................................. 200801858

(51) Int. Cl.
| A61B 17/58 | (2006.01) |
| A61B 17/60 | (2006.01) |
| A61F 2/00 | (2006.01) |
| A61C 8/00 | (2006.01) |

(52) U.S. Cl.
CPC ............. *A61C 8/0089* (2013.01); *A61C 8/0022* (2013.01)

(58) Field of Classification Search
CPC ................ A61C 8/0089; A61F 2/4611; A61F 2002/448
USPC .............. 606/99, 316; 433/146, 152; 411/386
See application file for complete search history.

(56) References Cited

U.S. PATENT DOCUMENTS

| 413,968 | A | * | 10/1889 | Rogers .......................... 411/386 |
| 2,210,349 | A | | 8/1940 | Beeck et al. |
| 3,702,028 | A | | 11/1972 | Edelman et al. |
| 4,834,081 | A | | 5/1989 | Van et al. |
| 6,019,602 | A | | 2/2000 | Fletcher et al. |
| 6,585,740 | B2 | * | 7/2003 | Schlapfer et al. ............. 606/308 |
| 2005/0250073 | A1 | | 11/2005 | Tresser et al. |
| 2008/0227057 | A1 | * | 9/2008 | Anitua Aldecoa ............ 433/174 |

FOREIGN PATENT DOCUMENTS

| ES | 289364 U | 10/1986 |
| ES | 2103196 A1 | 8/1997 |
| WO | WO 2006088291 A1 | 8/2006 |

* cited by examiner

*Primary Examiner* — David Bates
*Assistant Examiner* — Olivia C Chang
(74) *Attorney, Agent, or Firm* — Browdy and Neimark, PLLC

(57) ABSTRACT

Implant removal tool (1) which allows removing an implant (5) from a patient's bone (6). The implant removal tool (1) comprises a head (2), to which a torque-providing system is attached, and a threaded body (4) preferably with a decreasing diameter. The threaded body (4) preferably has a thread to the left and is intended to be threaded into the hole (7) of the implant (5). The extraction of the implant (5) is relatively simple to carry out, removing the implant (5) in an almost clean manner and leaving a very small cavity (13) in the patient's bone (6). Therefore, the implant removal tool (1) according to the invention makes the removal of an implant (5) a far less traumatic procedure for the patient.

4 Claims, 3 Drawing Sheets

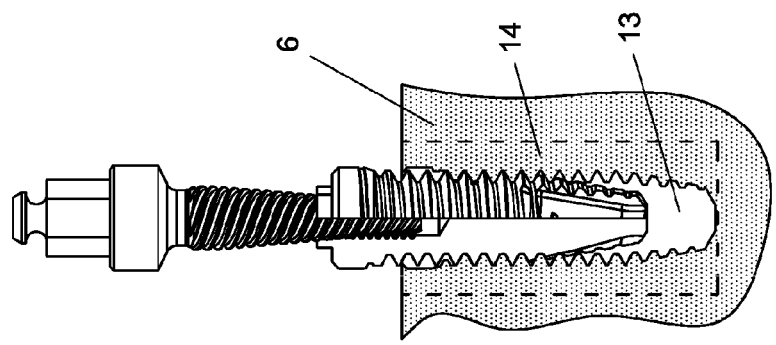
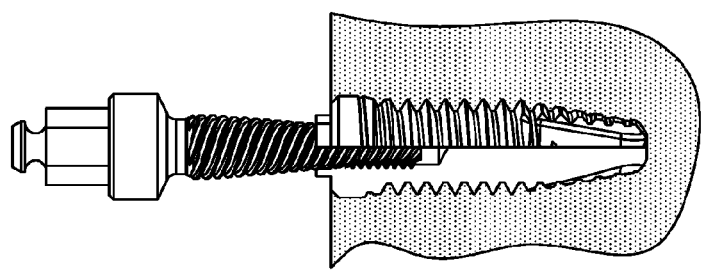
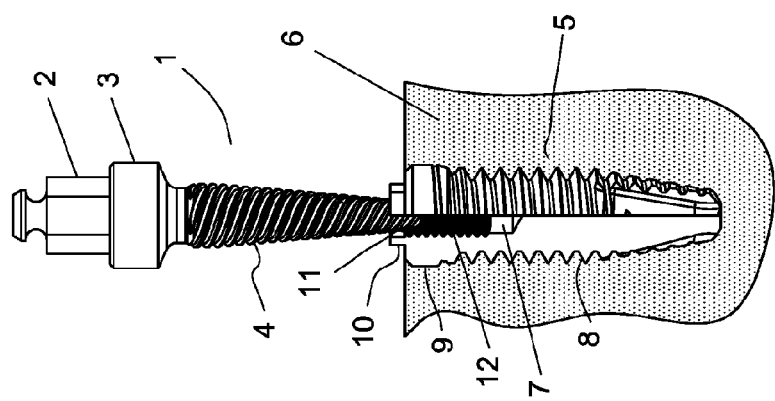
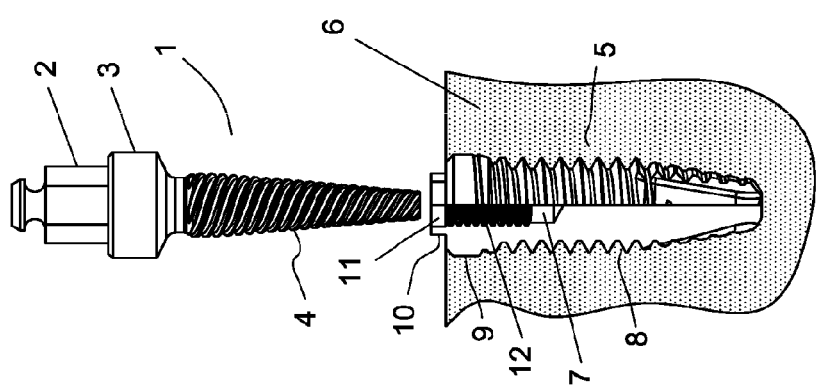

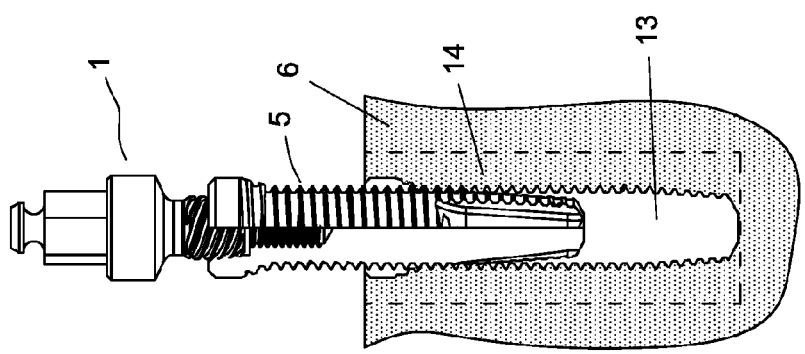
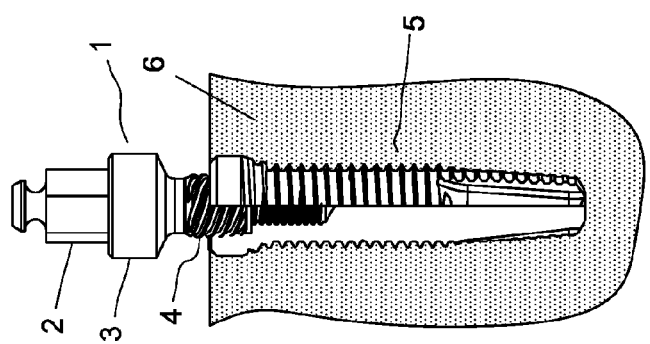
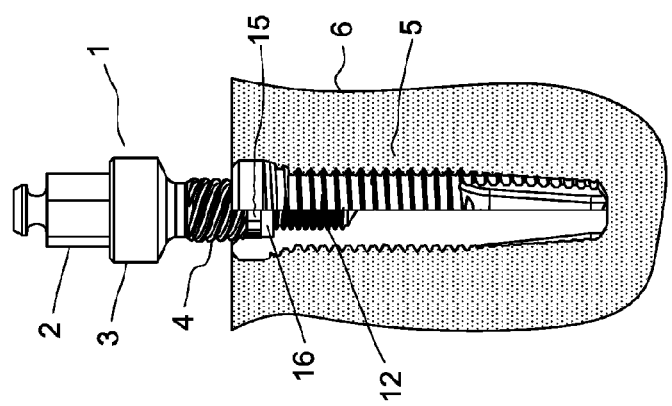
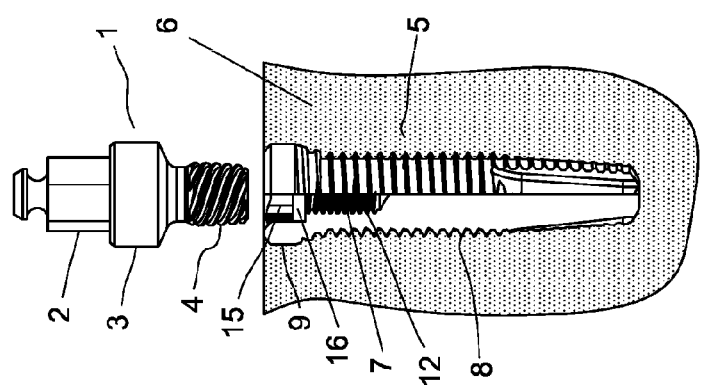

IMPLANT EXTRACTION TOOL

FIELD OF THE INVENTION

The invention relates to a tool that enables an implant to be removed from a patient's bone, for example to remove a dental implant from a patient's mouth once this dental implant has been osseointegrated into the patient's maxillary bone or jawbone.

PRIOR ART

An implant is a piece that is inserted into an osseous cavity prepared in a patient's bone, and to which a prosthesis is later attached. The procedure for inserting an implant is usually the following: a cavity is drilled in the patient's bone to receive the implant; the implant is inserted into this cavity; a certain period of time passes until the implant is osseointegrated in the bone; once the implant has osseointegrated, the prosthesis may be attached to the implant using a screw or whatever applicable accessory.

Unfortunately, sometimes it is necessary to remove the implant once it has been inserted and osseointegrated. For example, it is necessary to remove the implant in the event of unwanted osseous losses, bone breakage or if the implant has been incorrectly positioned. The implant will also have to be removed if the prosthesis is modified and the implant is no longer valid or required to support it.

The removal of an implant is not an easy task as it is designed so that its connection to the bone is extremely robust, resistant to multi-directional forces and difficult to break. For example, in dental implantology, a dental implant must withstand repeated oclusal and masticatory forces with a magnitude of up to 700 N during its useful life.

Continuing with the example of dental implants, the most commonly used technique to remove a dental implant at present consists of drilling the bone around the implant with a hollow cylindrical drill, removing the dental implant along with a portion of the surrounding bone. This technique is obviously traumatic as it involves the removal of a large amount of bone and leaves a large cavity in the patient's bone. This cavity must then be filled and regenerated using appropriate bone regeneration techniques. Also, this cavity may be up to 30% larger in diameter than the diameter of the implant, which is equivalent to 70% greater bone volume. This means that a second implant of a much larger size will need to be inserted if the implant removed is to be replaced.

In general, the removal of any implant is traumatic.

The invention aims to offer a new tool that allows the removal of an implant in the least possible traumatic way for the patient's bone, using a removal procedure that is simple to carry out for the surgeon and with the least possible discomfort for the patient.

BRIEF DESCRIPTION OF THE INVENTION

The object of the invention is a tool that allows removal of an implant from a patient's bone, the implant being characterized by comprising external walls in contact with the bone and by comprising a hole. The hole is either originally provided in the implant or is carved in the implant prior to using the implant removal tool. The implant removal tool comprises a head and a threaded body. The head provides the means of attaching a system capable of providing torque to the implant removal tool, for example a surgical motor, a ratchet wrench, etc. The diameter of the threaded body is preferably decreasing. At some points, the diameter of the threaded body is greater than the diameter of the hole of the implant; the smallest diameter of the threaded body is smaller than the diameter of this hole. The threaded body is meant to be introduced in the hole of the implant and threaded (forcing a thread) into the internal walls of said hole. The threaded body has a decreasing diameter so that its end has a smaller diameter than the hole of the implant and the rest of the threaded area gains thickness and may be properly attached to the internal walls of the hole (which does not happen if the diameter is constant).

The operation of the implant removal tool is as follows. The implant removal tool is inserted into the hole of the implant (which may already exist or may be perforated prior to the extraction). The torque-providing system makes the implant removal tool turn. As the torque-providing system makes the implant removal tool turn, the implant removal tool is threaded into the hole of the implant, forcing the thread. As the system continues to turn, the threaded body of the implant removal tool tightens its attachment to the hole, so the tightening torque is applied to the external walls of the implant that are in contact with the bone. When the tightening torque exceeds a certain value, the turning of the torque-providing system forces the implant to break its connection with the bone, allowing it to be removed.

Preferably, the thread of the threaded body of the implant removal tool is to the left, to enable optimum operation with implants whose exterior walls are threaded (whereby the thread of this threaded part is generally to the right). In other words, the thread of the threaded body of the implant removal tool is in the opposite direction to the thread of the threaded part of the majority of implants fitted with a threaded part (for example the majority of dental implants). This embodiment will also be able to be used to remove implants not provided with an exterior thread.

Obviously, an embodiment in which the thread of the threaded body of the implant removal tool is to the right is also considered. This embodiment will generally be used to remove implants whose exterior thread is to the left, although it will also be able to be used to remove implants not provided with an exterior thread, for example.

In this case, the operation of the implant removal tool is as follows. First of all, the implant removal tool is inserted into the hole of the implant. The torque-providing system makes the implant removal tool turn in an anti-clockwise direction (towards the left). As the torque-providing system makes the implant removal tool turn, the implant removal tool is threaded into the hole of the implant, forcing the thread. As the system continues to turn, the threaded body of the implant removal tool tightens its attachment to the hole; in consequence, the tightening torque is then applied to the threaded part of the implant. When the tightening torque exceeds a certain value, the left (anti-clockwise) turn of the torque-providing system forces the implant to break its connection with the bone and begins unthreading the implant (as its threaded part is to the right). If the system continues turning to the left, the implant is unthreaded and is cleanly removed from the bone.

Implants are generally fitted with a hidden threaded hole onto which different parts such as a screw, healing abutment, etc. are attached. If so, the implant removal tool according to the invention will preferably be inserted into this hidden threaded hole.

The implant removal tool according to the invention can be used to remove many types of implants: dental implants, osteosynthesis screws, hollow implants, screws to attach osseous blocks, etc.

In the case of dental implants, surgical tests have proven that the implant removal tool according to the invention allows a dental implant to be removed in an almost perfectly-clean way (even in the case of removing dental implants with cylindrical and unthreaded exterior walls). On the other hand, using conventional tools, the removal procedure is far more complex and dangerous for the patient. Not only does it produce a final hole in the bone that is considerably larger (with the damage that this entails, as previously explained) but it is also risky. If the insertion with the conventional tool (trephine drill) is too deep, the dental nerve or the adjacent implants or teeth may be damaged. This risk is non-existent when using the tool according to the invention.

Furthermore, the implant removal tool of this invention allows another implant of the same size as the previous one (which is supposedly the most desirable size) to be inserted into the osseous cavity once the implant has been removed. Instead, if the definitive removal of the implant is desired, the small size of the bone cavity significantly improves the post-extraction scenario, notably reducing recovery time (time for full regeneration of the bone).

BRIEF DESCRIPTION OF THE FIGURES

The details of the invention can be appreciated in the accompanying figures, which do not intend to limit the scope of the invention:

FIGS. 1 to 4 show the removal sequence of a dental implant using a first embodiment of the implant removal tool according to the invention.

FIGS. 5 to 8 show the removal sequence of a dental implant using a second embodiment of the implant removal tool according to the invention.

DETAILED DESCRIPTION OF THE INVENTION

Figure 12:
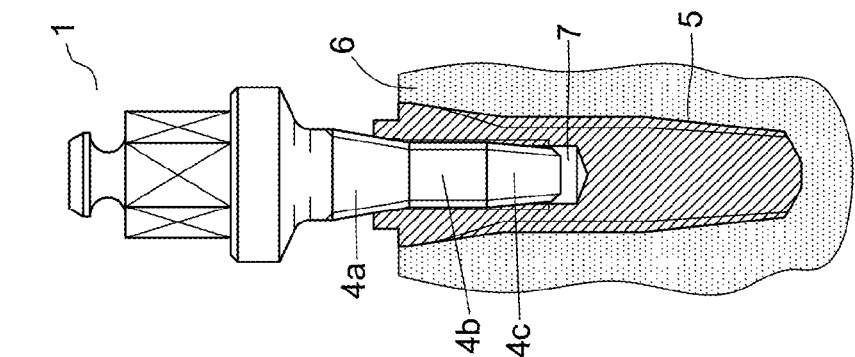

FIGS. 1 to 4 show the removal sequence of an implant, in this case a dental implant, using a first embodiment of the implant removal tool (1) according to the invention. As can be seen in the figures, the implant (5) comprises a threaded part (8) and a head (9). The threaded part (8) attaches the implant (5) to the bone (6). The head (9) allows the implant (5) to be attached to the prosthesis (false tooth). These figures show an implant (5) provided with an external connection; in other words, the head (9) has a protruding part, in this case a hexagonal protrusion (10), on which additional parts are placed in order to attach the prosthesis. The implant (5) comprises a hole (7), which in the figure is a blind threaded hole provided with a threaded area (12) and a cylindrical recess (11).

The implant removal tool (1) comprises a head (2) and a threaded body (4). The head (2) serves as a means of attaching a system capable of providing a torque to the implant removal tool (1). For example, the torque-providing system can be a surgical motor, a ratchet wrench, etc. The threaded body (4) is meant to be inserted in the hole (7) of the implant (5) and to be bound to the implant (5). The threaded body (4) has a threaded profile with a decreasing diameter which is capable of forcing its threading into the internal walls of the hole (7) of the implant (5). The minimum diameter of the threaded body (4) must therefore be less than the diameter of the hole (7). The thread of the threaded body (4) is to the left, which is opposite to that of the threaded part (8) of the implant (5). The implant removal tool (1) shown in these figures is specially designed to allow removing an implant (5) provided with an external connection: the threaded body (4) is long, capable of being threaded to both the cylindrical recess (11) and the threaded area (12) of the hole (7) of the implant (5).

Preferably, the implant removal tool (1) also comprises an unthreaded neck (3) positioned between the head (2) and the threaded body (4). This neck (3) must be extremely robust so as not to break when the torque-providing system turns the implant removal tool (1). It must be taken into account that when the implant removal tool (1) turns, it is subject to a lot of tension due to the fact that the threaded body (4) becomes bound to the hole (7) and the fact that the implant (5) breaks its threaded connection to the bone (6).

The threaded body (4) is preferably conical, for manufacturing simplicity (mechanized). However, the invention considers other different embodiments in which the profile of the threaded body (4) is decreasing or not.

The operation of the implant removal tool (1) is as follows. As can be seen in FIGS. 1 and 2, the implant removal tool (1) is inserted into the hole (7) of the implant (5). Initially, there is a certain gap between the implant removal tool (1) and the hole (7), as can be seen in FIG. 2. When the implant removal tool (1) reaches a limit (the gap disappearing), the torque-providing system is started so that it turns to the left (in an anti-clockwise direction). Then, the implant removal tool (1) begins to thread itself (forcing a thread) in the cylindrical recess (11) and in the threaded area (12), as shown in FIG. 3. If the torque-providing system continues turning, the implant removal tool (1) continues fitting into the hole (7). In consequence, the threaded connection between the implant removal tool (1) and the implant (5) is consolidated, or in other words, the implant removal tool (1) becomes bound to the implant (5). At the same time, the implant (5) begins to unthread from the bone (6). As shown in FIG. 4, if the system continues to be operated in an anti-clockwise direction, the implant (5) is continues to unthread from the bone (6) and is finally removed from the bone (6) leaving a cavity (13).

FIG. 4 also illustrates the cavity (14) that would remain if the removal of the implant (5) had been performed using a conventional method based on hollow cylindrical drills. This cavity (14) is far bigger than the cavity (13) obtained using the implant removal tool (1) and the method according to the invention.

FIGS. 5 to 8 show the removal sequence of an implant (5) using a second embodiment of the implant removal tool (1) according to the invention. In this case, the implant removal tool (1) is especially intended to allow the removal of an implant (5) with an internal connection, i.e., fitted with a hole (7) that comprises an anti-rotational area (15) and a cylindrical area (16) in addition to the aforementioned threaded area (12). In this case, the threaded body (4) of the implant removal tool (1) has a short length, as it is suffice for the threaded body (4) to thread into the anti-rotational area (15) and the cylindrical area (16) for the implant removal tool (1) to correctly remove the implant (5).

Figure 11:
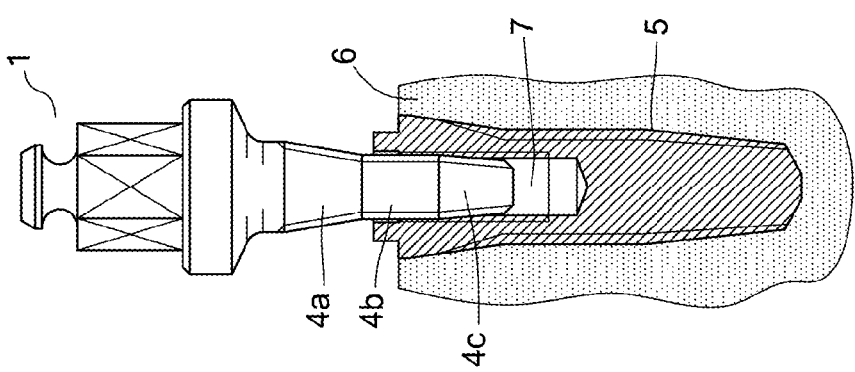
FIGS. 10, 11 y 12 show a sequence of how the implant removal tool of FIG. 9 is inserted in a dental implant.
Figure 10:
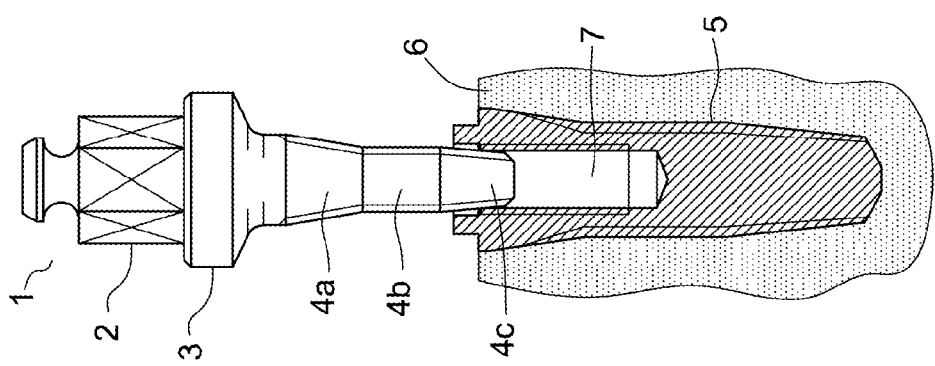
Figure 9:
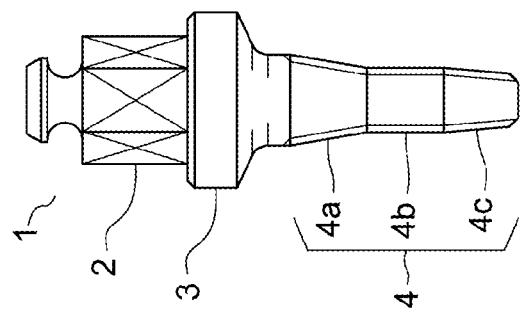
FIG. 9 shows another embodiment of the implant removal tool according to the invention.

FIG. 9 shows another embodiment of the implant removal tool (1) according to the invention. According to this embodiment, the threaded body (4) comprises a first decreasing-diameter-provided threaded area (4a), a cylindrical threaded area (4b) whose diameter is greater than the internal diameter of the hole (7) of the implant (5) (said hole (7) being threaded in the present embodiment), and a second decreasing-diameter-provided threaded area (4c). FIGS. 10, 11 y 12 show a sequence of how the implant removal tool (1) of FIG. 9 is inserted in a dental implant (5). The second decreasing-diameter-provided threaded area (4c) helps begin insertion and start the threading of the implant removal tool (1) in the hole (7) of the implant (5), as shown in FIG. 10. As the implant removal tool (1) is threaded inside the implant (5), the cylindrical threaded area (4b) begins to thread as shown in FIG. 11. Because the diameter of the cylindrical threaded area (4b) is greater than the internal diameter of the hole (7), the cylindrical threaded area (4b) progressively erodes the implant (5), driving a new thread and threading itself into this new thread. The cylindrical threaded area (4b) therefore provides an axial guiding of the implant removal tool (1) along the implant (5). Finally, if the implant removal tool (1) is further threaded inside the implant (5) as shown in FIG. 12, the first decreasing-diameter-provided threaded area (4a) begins to thread in the hole (7) of the implant (5) applying a horizontal traction on the internal walls of said hole (7). When traction is sufficiently high, the friction and the threading between the first decreasing-diameter-provided threaded area (4a) and the walls of the hole (7) increase until the implant removal tool (1) can no longer be turned inside the hole (7) and the torque is transferred to the implant (5), eventually forcing the connection between the implant (5) and the bone (6) to break (if not yet broken) and the implant (5) to be unscrewed from the bone (6). In the present embodiment, the breakage torque is applied by the part of the threaded body (4) provided with a greater diameter, i.e., by the first decreasing-diameter-provided threaded area (4a).

In the present embodiment, the extraction torque is to be applied by an area provided with a high diameter (the aforementioned first decreasing-diameter-provided threaded area (4a)). Therefore, because it is a larger (and therefore more robust) area that is responsible for applying the extraction torque and because the contact surface between the implant removal tool (1) and the implant (5) is larger, the risk of breaking the implant removal tool (1) during usage is low and, at the same time, a greater torque can be applied on the implant (5), it therefore being easier to break the connection between the implant (5) and the bone (6).

Preferably, the first decreasing-diameter-provided threaded area (4a) and/or the second decreasing-diameter-provided threaded area (4c) are conical-shaped, as this is the most simple and equally effective embodiment.

The invention claimed is:

1. An implant and implant removal tool assembly comprising:
    an implant (5) comprising a hole (7) and an outer threaded portion, wherein said outer threaded portion is arranged in a first handedness; and
    an implant removal tool (1) to enable removal of said implant (5), said implant configured to be osseointegrated to a patient's bone, said implant removal tool (1) comprising:
        a head (2), to which a system capable of providing torque to the implant removal tool (1) is to be attached,
        an unthreaded neck connected at a first end to one end of the head, and
        a threaded body (4) connected at a first end to a second end of the unthreaded neck, and having a second end configured to be inserted into the hole (7) of the implant (5), wherein the threaded body (4) is arranged in a second handedness opposite to said first handedness and consists only of,
            in a position extending directly from the second end of the unthreaded neck, a first threaded area (4a) having a constantly decreasing outermost diameter corresponding to peaks of a thread of said first threaded area (4a), and a constantly decreasing innermost diameter corresponding to valleys of said thread of said first threaded area (4a),
            in a position extending directly from the first threaded area (4a), a second threaded area (4b) having a constant outermost diameter corresponding to peaks of a thread of said second threaded area (4b), and a constant innermost diameter corresponding to valleys of said thread of said second threaded area (4b), wherein said innermost diameter in the second threaded area is greater than the internal diameter of the hole (7) of the implant (5), and
            in a position extending directly from the second threaded area (4b), a third threaded area (4c) having a constantly decreasing outermost diameter corresponding to peaks of a thread of said third threaded area (4c), and a constantly decreasing innermost diameter corresponding to valleys of said thread of said third threaded area (4c).

2. The implant and implant removal tool assembly of claim 1, wherein said first handedness of said outer threaded portion of said implant is a clockwise direction, and said second handedness of said threaded body (4) is a counter-clockwise direction.

3. The implant and implant removal tool assembly of claim 1, wherein said first handedness of said outer threaded portion of said implant is a counter-clockwise direction and said second handedness of said threaded body (4) is a clockwise direction.

4. The implant and implant removal tool assembly of claim 1, wherein the first threaded area (4a) and/or the third threaded area (4c) is conical-shaped.

* * * * *